US008706248B2

(12) United States Patent
van Dijk et al.

(10) Patent No.: US 8,706,248 B2
(45) Date of Patent: Apr. 22, 2014

(54) DIRECTIONAL SOUND PROCESSING IN A COCHLEAR IMPLANT

(71) Applicants: Bastiaan van Dijk, Mechelen (BE); Ernst L. von Wallenberg, Muelheim (DE); Kyriaky Griffin, Castle Hill (AU)

(72) Inventors: Bastiaan van Dijk, Mechelen (BE); Ernst L. von Wallenberg, Muelheim (DE); Kyriaky Griffin, Castle Hill (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/645,842

(22) Filed: Oct. 5, 2012

(65) Prior Publication Data
US 2013/0184784 A1 Jul. 18, 2013

Related U.S. Application Data

(63) Continuation of application No. 11/482,709, filed on Jul. 10, 2006, now Pat. No. 8,285,383.

(60) Provisional application No. 60/697,730, filed on Jul. 8, 2005.

(51) Int. Cl.
*A61N 1/00* (2006.01)
*A61B 5/04* (2006.01)

(52) U.S. Cl.
USPC .................. 607/57; 607/55; 607/56; 600/372

(58) Field of Classification Search
USPC ...................... 607/55–57; 600/372
See application file for complete search history.

(56) References Cited

U.S. PATENT DOCUMENTS

| 5,571,148 A | 11/1996 | Loeb et al. |
| 5,597,380 A | 1/1997 | McDermott et al. |
| 5,793,785 A | 8/1998 | Nakanishi et al. |
| 5,793,875 A | 8/1998 | Lehr et al. |
| 5,999,856 A | 12/1999 | Kennedy |
| 6,205,360 B1 | 3/2001 | Carter et al. |
| 6,222,927 B1 * | 4/2001 | Feng et al. .................. 381/94.2 |
| 6,480,820 B1 | 11/2002 | Clopton et al. |
| 6,565,503 B2 | 5/2003 | Leysieffer et al. |
| 6,603,858 B1 | 8/2003 | Raicevich et al. |
| 6,697,674 B2 | 2/2004 | Leysieffer |

(Continued)

FOREIGN PATENT DOCUMENTS

| EP | 1841281 | 10/2007 |
| WO | 97/40645 | 10/1997 |

(Continued)

OTHER PUBLICATIONS

Yao et al., "Blind Beamforming on a Randomly Distributed Sensor Array System", IEEE Journal on Selected Areas in Communications, vol. 16, No. 8, Oct. 1998, pp. 1555-1567 (13 pages).

*Primary Examiner* — Nicole F Lavert
(74) *Attorney, Agent, or Firm* — K&L Gates, LLP

(57) ABSTRACT

A cochlear implant implementing a directional sound processing system is provided. Specifically, the cochlear implants implementing the present invention comprise a plurality of audio sensors arranged in at least one external component of the cochlear implant to spatially receive ambient sound. At least one audio sensor is located in one of the external components of the cochlear implant, while one other audio sensor is located elsewhere, such as in a component other than the first component. The cochlear implant includes an directional sound processor comprising an array processor and a sound processor to convert the received sounds into a cochlea stimulation instruction signal.

20 Claims, 8 Drawing Sheets

(56) References Cited

U.S. PATENT DOCUMENTS

| | | |
|---|---|---|
| 6,888,949 B1 | 5/2005 | Vanden Berghe et al. |
| 2001/0031996 A1 | 10/2001 | Leysieffer |
| 2001/0049466 A1 | 12/2001 | Leysieffer et al. |
| 2003/0069626 A1 | 4/2003 | Lattner et al. |
| 2004/0202339 A1* | 10/2004 | O'Brien et al. ............... 381/312 |
| 2005/0010267 A1 | 1/2005 | Ibrahim |
| 2006/0217784 A1 | 9/2006 | Kitazawa et al. |
| 2007/0043403 A1 | 2/2007 | Blamey et al. |

FOREIGN PATENT DOCUMENTS

| | | |
|---|---|---|
| WO | 2005/006808 | 1/2005 |
| WO | 2005/048648 | 5/2005 |
| WO | 2005/110530 | 11/2005 |

* cited by examiner

DIRECTIONAL SOUND PROCESSING IN A COCHLEAR IMPLANT

CROSS-REFERENCE TO RELATED APPLICATIONS

The present application is a continuation application of U.S. patent application Ser. No. 11/482,709 filed Jul. 10, 2006, now U.S. Pat. No. 8,285,383 issued Oct. 9, 2012, which claims benefit of U.S. Provisional Patent Application No. 60/697,730 filed Jul. 8, 2005, which is hereby incorporated by reference herein.

BACKGROUND

1. Field of the Invention

The present invention relates generally to sound processing, and more particularly, to directional sound processing in a cochlear implant.

2. Related Art

Hearing loss, which may be due to many different causes, is generally of two types, conductive and sensorineural. Conductive hearing loss occurs when the normal mechanical pathways which provide sound to hair cells in the cochlea are impeded, for example, by damage to the ossicles. Conductive hearing loss is often addressed with conventional auditory prostheses, commonly referred to as hearing aids, which amplify sound so that acoustic information may reach the cochlea.

Profound deafness, however, is caused by sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to, or absence of, the mechanism that naturally generates nerve impulses from sound. As a result, prosthetic hearing implants such as cochlear prostheses (commonly referred to as cochlear prosthetic devices, cochlear implants, cochlear devices, and the like; simply "cochlear implants" herein) have been developed to provide persons with sensorineural hearing loss with the ability to perceive sound.

Cochlear implants typically comprise one or more external components worn by the patient (also referred to as recipient, user, wearer and the like; "recipient" herein) and internal components that are implanted in the recipient. The external and internal components cooperate with each other to provide sound sensations to the recipient.

The external component(s) traditionally comprise several integrated or physically separate elements generally including one or more acoustical transducers that sense ambient sounds, a sound processor that selects and converts certain detected sounds, particularly speech, into coded signals, a power source such as a battery, and an external transmitter antenna.

The internal components traditionally comprise several integrated or physically separate elements generally including a receiver antenna, a stimulator unit and a carrier member on which an electrode assembly is disposed for stimulating the recipient's auditory nerve. The coded signals generated by the sound processor are transmitted transcutaneously from the external transmitter antenna to the implanted receiver antenna, commonly located within a recess of the temporal bone of the recipient. In addition to coded sound signals, this communication link is often used to transmit power to the implanted stimulator unit. Conventionally, this communication link has been in the form of a radio frequency (RF) link, although other communication and power links have been proposed and implemented with varying degrees of success.

The stimulator unit processes the coded signal and generates an electrical stimulation signal to the intra-cochlea electrode array. The electrode array typically has a plurality of electrodes that apply electrical stimulation to the auditory nerve to produce a hearing sensation corresponding to the original detected sound. Because the cochlea is partitioned into regions each responsive to stimulation signals in a particular frequency range; i.e., tonotopically mapped, each electrode of the implantable electrode array delivers a stimulation current to a particular region of the cochlea. In the conversion of sound to electrical stimulation, frequencies are allocated to stimulation channels that provide stimulation current to electrodes positioned in the cochlea at or immediately adjacent to the region of the cochlear that would naturally be stimulated in normal hearing. This enables cochlear implants to bypass the hair cells in the cochlea to directly deliver electrical stimulation to auditory nerve fibers, thereby allowing the brain to perceive hearing sensations resembling natural hearing sensations.

SUMMARY

In one aspect of the present invention, a cochlear implant system is disclosed. The cochlear implant system comprises: a behind the ear (BTE) sound processing unit; a cable; a transmit unit connected to said BTE by said cable and configured to transmit signals from said BTE to an internal component of said cochlear implant; a plurality of spatially-arranged audio sensors, configured to receive ambient sound, and comprising any combination of: a sensor located in said BTE, a sensor located in said transmit unit, and a sensor located in said cable; and a directional sound processor having an array-processing stage configured to generate a directional sound signal from sound received by a first one of said plurality of sensors, and wherein said directional sound processor is configured to combine said directional sound signal and a signal representative of sound received by a second one of said plurality of sensors to generate a processed sound signal from which sound received from non-desired directions is attenuated.

In another aspect of the present invention, a cochlear implant system is disclosed. The cochlear implant system comprises a behind the ear BTE sound processing unit; a cable; a transmit unit connected to said BTE by said cable and configured to transmit signals from said BTE to an internal component of said cochlear implant wherein each of the BTE, the cable and the transmit unit are comprised in a single cochlear implant.

In another aspect of the present invention, a cochlear implant system is disclosed. The cochlear implant system comprises a behind the ear BTE sound processing unit; a cable; a transmit unit connected to said BTE by said cable and configured to transmit signals from said BTE to an internal component of said cochlear implant wherein the cochlear implant system comprises a single cochlear implant.

In another aspect of the present invention, a cochlear implant having a plurality of physically separate external components is disclosed. The cochlear implant comprises: a plurality of audio sensors spatially-arranged on the external components to receive ambient sound, each audio sensor comprising at least one acoustical transducer, wherein at least one of the plurality of audio sensors is disposed in a first of the external components and a second of the plurality of audio sensors is disposed in a second of the external components.

In another aspect of the present invention, a cochlear implant is disclosed. The cochlear implant comprises: a plurality of spatially-arranged audio sensors each comprising one or more acoustical transducers; and a directional sound processor configured to process sound received by the audio sensors from a desired direction, and to attenuate sound received from other directions.

In a further aspect of the present invention, a method for delivering stimulation signals to a recipient's cochlea representing sound received from a desired direction. The method comprises: receiving ambient sounds at a plurality of audio sensors spatially-arranged on a plurality of external components of a cochlear implant; and processing sound received by at least some of the plurality of audio sensors from a desired direction and attenuating sound received from directions other than said desired direction.

BRIEF DESCRIPTION OF THE DRAWINGS

Embodiments of the present invention are described below in conjunction with the accompanying drawings, in which.

DETAILED DESCRIPTION

Aspects of the present invention are generally directed to a cochlear implant implementing a directional sound processing system. A directionally-sensitive cochlear implant of the present invention comprises a plurality of audio sensors spatially-arranged to receive ambient sound. At least one audio sensor is disposed in one of the external components of the cochlear implant, while at least one other audio sensor is located elsewhere, such as in an external component other than the first component. Each audio sensor comprises at least one acoustical transducer such as a microphone.

Such cochlear implants also include a directional sound processor that processes sound received from a desired direction ("desired sounds") and eliminates or attenuates sound received from other directions ("undesired sounds").

Embodiments of the directional sound processor comprise an array processor composed of one or more array-processing stages. Each array-processing stage generates a directional sound signal by adaptively enhancing the sensitivity of one or more associated sensors to the desired sounds, essentially treating undesired sound as noise. The desired direction is determined based on, for example, the amplitudes of the incident ambient sounds or other conditions or settings. By increasing the signal-to-noise ratio (SNR), the directional sound signal is an enhanced representation of the ambient sound incident on the plurality of sensors from the desired direction. The directional sound signal is converted to a stimulation instruction signal by a sound processor.

The present invention will be described principally in the context of cochlear implants. However, it will be appreciated by those skilled in the art that the same principles are readily implemented in other applications.

Figure 1:
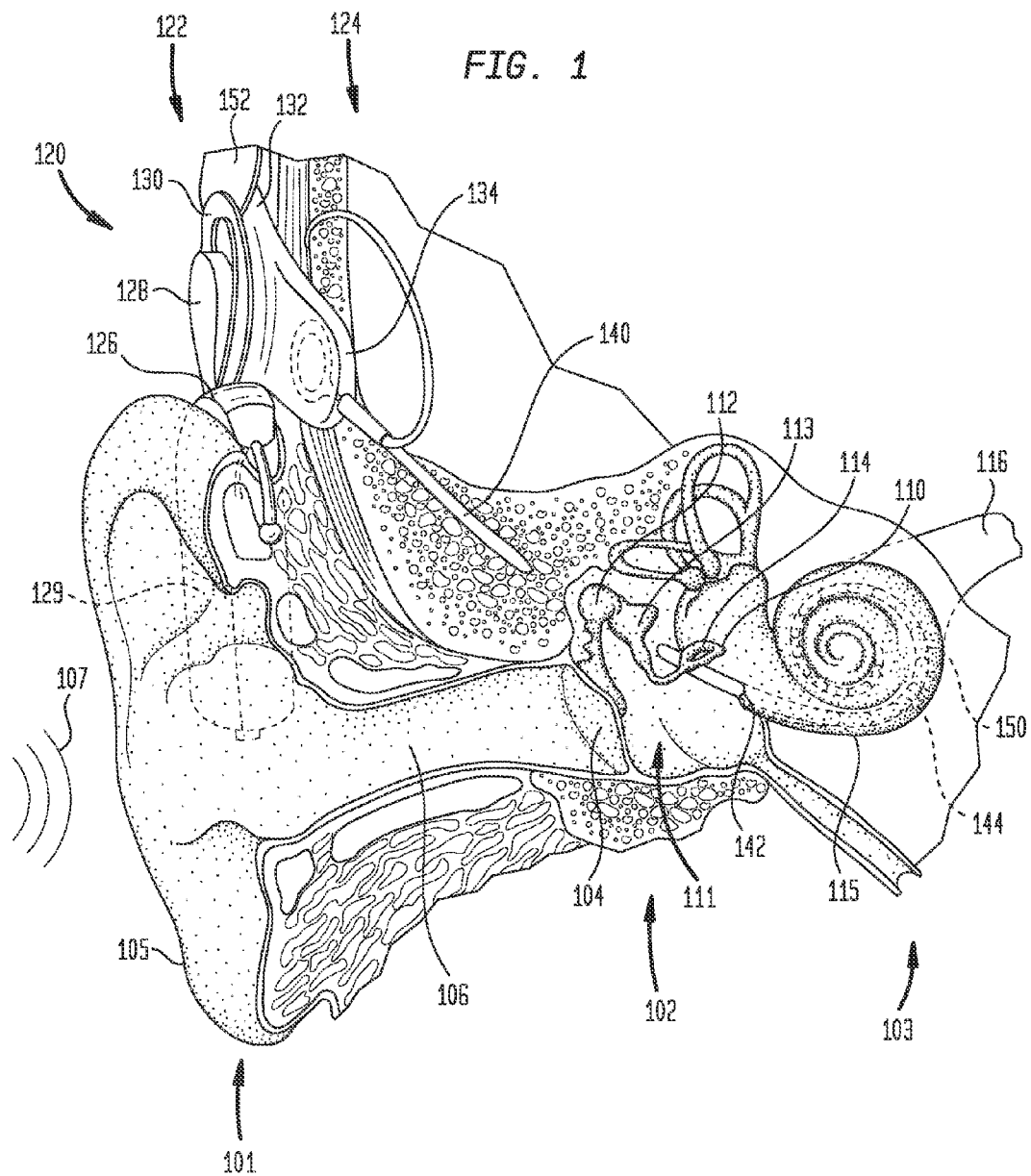
FIG. 1 is a perspective view of an exemplary cochlear implant in which embodiments of the present invention may be advantageously implemented.

FIG. 1 is a perspective view of an exemplary cochlear implant 120 in which embodiments of the present invention may be advantageously implemented. In fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells and auditory nerve 116 to the brain (not shown), where they are perceived as sound. In deaf persons, there is an absence or destruction of the hair cells. A cochlear implant 120 is utilized to directly stimulate the ganglion cells to provide a hearing sensation to the recipient.

FIG. 1 also shows how a cochlear implant 120 is positioned in relation to outer ear 101, middle ear 102 and inner ear 103. Cochlear implant 120 comprises external component assembly 122 which is directly or indirectly attached to the body of the recipient, and an internal component assembly 124 which is temporarily or permanently implanted in the recipient. External assembly 122 comprises several components including a plurality of audio sensors spatially arranged on external components 122 of cochlear implant 120 for detecting sound. The spatial arrangement of the plurality of audio sensors is described in greater detail below.

Sound processor 126 is a directional sound processor configured to generate coded stimulation control signals representing sound detected by the plurality of audio sensors from a desired direction. These coded signals are then provided to an external transmitter unit 128. In the embodiment shown in FIG. 1, sound processor 126 is a behind the ear (BTE) sound processing unit. The BTE is constructed and arranged so that it can fit behind the outer ear 101 of a recipient. BTE may include a power source to power all elements of the cochlear implant, such as the external coil. In certain embodiments, the power source may be physically disconnected from the BTE, thereby causing the BTE to discontinue operation. Furthermore, in other embodiments, accessories may be connected to the BTE to add additional functionality.

It would be appreciated by one of ordinary skill in the art that sound processor 126 may also comprise a body-worn sound processor, a modular sound processor or a sound processor headset. Details of the sound processing performed in sound processor 126 in accordance with embodiments of the present invention are discussed below.

External transmitter unit 128 comprises an external coil 130 and, preferably, a magnet (not shown) secured directly or indirectly in external coil 130. External transmitter unit 128 is configured to transmit the coded signals from sound processor 126, along with power from a power source 129 such as a battery to internal components 124 through tissue 152.

Internal components 124 comprise an internal receiver unit 132 having an internal coil (not shown) that receives and transmits power and coded signals received from external assembly 122 to a stimulator unit 134 to apply the coded signal to cochlea 115 via an implanted electrode assembly 140. Electrode assembly 140 enters cochlea 115 at cochleostomy region 142 and has one or more electrodes 150 positioned to be substantially aligned with portions of tonotopically-mapped cochlea 115. Signals generated by stimulator unit 134 are typically applied by an array 144 of electrodes 150 to cochlea 115, thereby stimulating auditory nerve 116.

Figure 2:
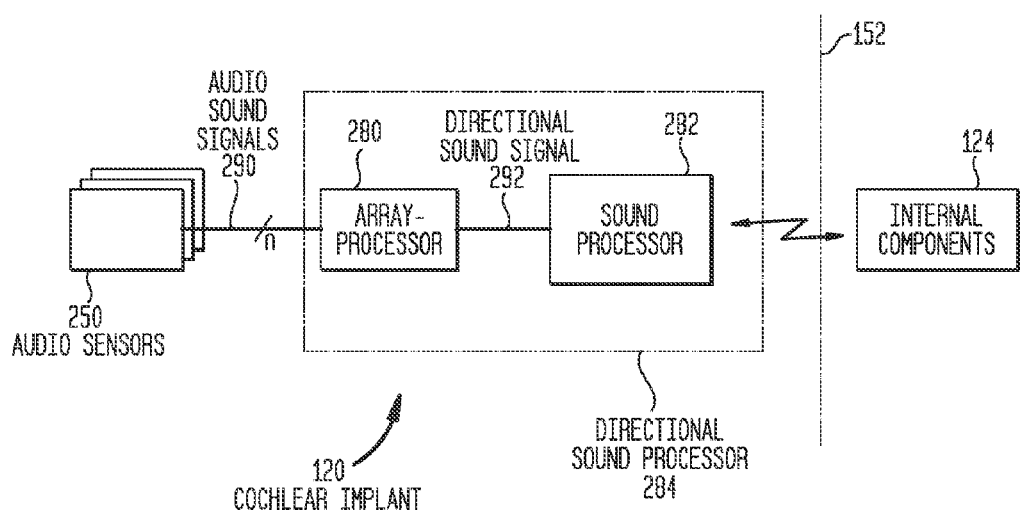
FIG. 2 is a schematic block diagram of selected components of a cochlear implant, in accordance with embodiments of the present invention.

FIG. 2 is a schematic block diagram of cochlear implant 120 illustrated in FIG. 1 in accordance with one embodiment of the present invention. Cochlear implant 120 comprises internal components 124 and external components 122 as described above with reference to FIG. 1. In the exemplary implementation shown in FIG. 2, only a portion of external components 122 is shown. In this embodiment, the portion of external components 122 shown comprises audio sensors 250 and an directional sound processor or system 284.

As noted, the audio sensors 250 are spatially-arranged in a plurality of external components of cochlear implant 120 to receive ambient sound. As used in this context, the term "spatially-arranged" refers to a distributed arrangement of audio sensors to receive sound from a plurality of directions. This is described in greater detail below.

In some embodiments, at least one audio sensor is located in one of the external components of the cochlear implant such as BTE or, while at least one other audio sensor is located elsewhere, such as in an external component other than the first external component. In certain embodiments, audio sensors 250 are further configured to deliver the sound sensed by the plurality of audio sensors to directional sound processor 284 as one or more received audio sound signals 290. In additional embodiments discussed below, sound received by a sensor is transmitted to directional sound processor 284 as a sensor-specific directional sound signal. Received audio sound signals 290 may be transferred to directional sound processor 284 via a cable or via a wireless means. Audio sensors 250 and directional sound processor 284 are described in greater detail below.

In accordance with aspects of the present invention, directional sound processor 284 comprises an array processor 280 composed of one or more array-processing stages (described below) and a sound processor 282. Each array-processing stage executes an array-processing algorithm to manipulate the ambient sounds provided by one or more audio sensors 250 to generate a directional sound signal 292. The application of the array-processing algorithm to received audio sound signals 290 results in a directional sound signal 292 in which sound components from a desired direction have an increased signal-to-noise ratio (SNR) while sound components from other directions are being attenuated. In embodiments of the present invention, array-processing implemented by array-processor 280 may include the initial delaying and summing of sensor inputs, as well as any adaptive filtering or other signal processing techniques associated with processing array signals. Details of the array-processing implemented in the present invention are described below with reference to FIG. 9.

Directional sound processor 284 is configured to process sound received from a desired direction and eliminates, cancels, filters, removes, or otherwise attenuates sound received from other directions. As noted above, directional sound processor 284 comprises an array processor composed of one or more array-processing stages, wherein each array-processing stage generates a directional sound signal by adaptively enhancing the sensitivity of the system to sounds from desired directions ("desired sounds"), essentially treating sound from other undesired directions as noise. Sound processor 282 converts the directional sound signal to a stimulation instruction signal. These coded stimulation instruction signals are then delivered to internal components 124 through tissue 152. Sound processor 282 may employee a sound processing scheme traditionally implemented in cochlear implants to convert a single sound to a stimulation instruction signal. For example, sound processor 282 may implement the processing schemes as described in U.S. Pat. Nos. 5,597,380 or 6,480,820, which are hereby incorporated by reference herein.

Figure 3:
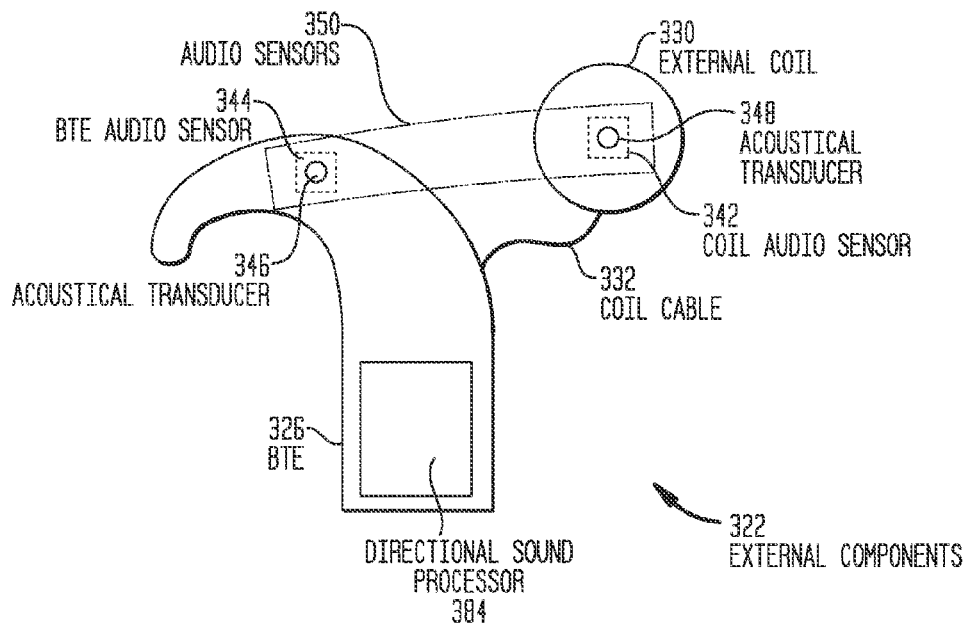
FIG. 3 is a simplified perspective view of the external components of a cochlear implant, in accordance with one embodiment of the present invention.

Specific embodiments of external component(s) 122 implementing different configurations of audio sensors 250 will now be described with reference to FIGS. 3-8. FIG. 3 is a schematic diagram of external components 122 illustrated in FIG. 1 and introduced above, in accordance with one embodiment of the present invention. In this exemplary embodiment, external components 122 are referred to herein as external components 322, while audio sensors 250 are referred to as audio sensors 350. External components 322 comprise BTE 326 connected to an external coil 330 via cable 332. BTE 326 is a sound processor worn behind the ear that contains all the physical elements required to process sound and generate an appropriate signal to send to external coil 330. BTE 326 includes an embodiment of directional sound processor 284, referred to herein as directional sound processor 384.

In this embodiment, audio sensors 350 comprise two audio sensors spatially-arranged to receive ambient sound. One sensor, referred to as BTE audio sensor 344, is disposed in BTE 326. The second sensor is located in external coil 330, and is referred to as coil audio sensor 342. In this illustrative embodiment, coil audio sensor 342 is located at the approximate center of external coil 130. It would be appreciated by one of ordinary skill in the art, however, that the location of BTE sensor 344 and coil sensor 342 are not restricted to the positions shown in FIG. 3.

As noted, each audio sensor may comprise one or more acoustical transducers. In this embodiment, BTE audio sensor 344 comprises a single acoustical transducer 346, shown as a microphone in FIG. 3. Similarly, in this embodiment, coil audio sensor 342 comprises a single acoustical transducer 348, also shown as a microphone. Either or both acoustical transducers 346 and 348 may possess a directional or omnidirectional polar response.

Audio sensors 342 and 344 receive ambient sound incident on their respective acoustical transducers 346 and 348, respectively. In the embodiment shown, each microphone 346 and 348 transmits its received sound to directional sound processor 384 in BTE 326. Directional sound processor 384 converts the received sounds to a coded stimulation instruction signal as introduced above and described in further detail below with reference to FIG. 9.

As noted above, external coil 330 receives processed sounds from BTE 326 and transmits these sounds to internal components 124.

It would be appreciated by one of ordinary skill in the art that sound processor 326 is not limited to a BTE sound processor configuration. In other embodiments, sound processor 326 is a modular processor. A modular sound processor contains a number of physical modules, which when interconnected together perform the complete processing required for implementing a cochlear implant.

Figure 4:
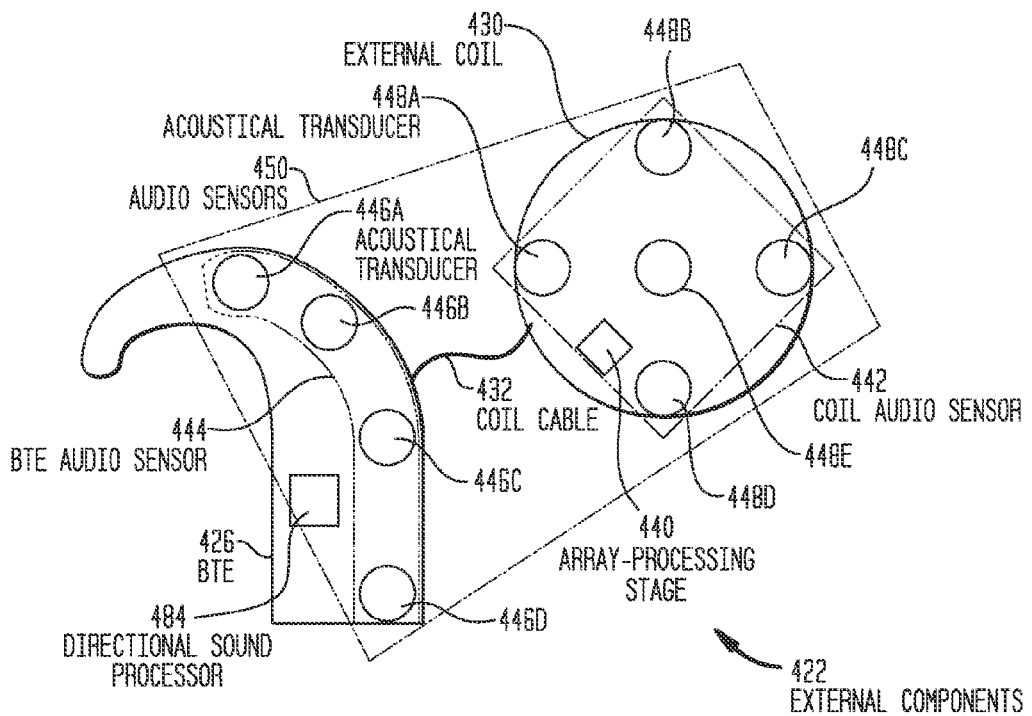
FIG. 4 is a simplified perspective view of the external components of a cochlear implant, in accordance with another embodiment of the present invention.

FIG. 4 is a schematic diagram of another embodiment of external components 122 introduced above with reference to FIG. 1, referred to herein as external components 422. In the embodiment shown in FIG. 4, external components 422 comprise an embodiment of BTE sound processor 126, referred to herein as BTE 426 and an embodiment of external coil 130, referred to herein as external coil 430. BTE sound processor 426 is connected to external coil 430 via coil cable 432.

In this embodiment of the present invention, external components 422 comprise audio sensors 450 spatially-arranged across BTE 426 and external coil 430 to receive ambient sounds. Audio sensors 450 residing on BTE 426 are collectively referred to as BTE audio sensor 444 while the acoustical transducers residing on external coil 430 are collectively referred to as coil audio sensor 442.

In this embodiment, BTE audio sensor 444 comprises four acoustical transducers 446A-446D. The quantity of acoustical transducers 446 in BTE sensor 444 may depend on various factors including the particular mechanical design of BTE 426, the particular type of technology used to realize acoustical transducers 446, the desired characteristics of audio sensor 444, and other factors.

Coil audio sensor 442 comprises five acoustical transducers 448A-448E. Here too, the quantity of acoustical transducers 448 may depend on various factors including the particular mechanical design of external coil 430, the particular type of technology used to realize acoustical transducers 448, the desired characteristics of audio sensor 442, and other factors.

One or more acoustical transducers 446 and 448 may possess a directional or omni-directional polar response. In certain embodiments, microphone 448E is disposed at the center of external coil 430 and has an omni-directional polar response. Furthermore, in certain embodiments, audio sensor 450 may be composed of identical acoustical transducers or combinations of different types of acoustical transducers.

BTE 426 implements an embodiment of directional sound processor 284, referred to herein as directional sound processor 484, to process sounds received by audio sensors 450. Audio sensors 444 and 442 are spatially-arranged to receive ambient sound with their respective microphones 446 and 448. In certain embodiments, each microphone 446 and 448 transmits its received sound to directional sound processor 484 disposed in BTE 426. Directional sound processor 484 converts the plurality of received sounds into a coded stimulation instruction signal as described below with reference to FIG. 9.

In alternative embodiments, directional sound processor 484 is configured to treat all acoustical transducers located in a particular sensor as a single transducer. In such an embodiment, the particular sensor, or the component on which the sensor is located, or directional sound processor 484 may further comprise an array-processing stage. As described below with reference to FIG. 9, an array-processing stage mathematically combines the audio signals generated by acoustical transducer(s) residing in the particular audio sensor to generate a directional sound signal for that sensor. Such a directional sound signal for a particular audio sensor is referred to herein as a sensor-specific directional sound signal. Such a sensor-specific directional sound signal is then transmitted to directional sound processor 484 for additional processing as described below with reference to FIG. 9.

For example, in the embodiment illustrated in FIG. 4, coil audio sensor 442 may further comprise an array-processing stage 440. Array-processing stage 440 functions as described below to convert the plurality of sounds received by acoustical transducers 448A-448E into a sensor-specific directional sound signal. Coil audio sensor 442 then transmits this sensor-specific directional sound signal to directional sound processor 484. Directional sound processor 484 uses sensor-specific directional sound signal from coil audio sensor 442 and one or more received sounds from BTE audio sensor 444 to generate a stimulation instruction signal corresponding to the sound incident on sensors 450 from a desired direction, as described below with reference to FIG. 9.

In other embodiments, directional sound processor 484 comprises an array-processor having a plurality of array-processing stages. In this embodiment, a plurality of received sounds from a single audio sensor is converted to a sensor-specific directional sound signal by one of the array-processing stages. Another array-processing stage then utilizes this sensor-specific directional sound signal, as well as the received sounds from the remaining audio sensors to generate a directional sound signal corresponding to the sounds from all audio sensors. It would be appreciated by one of ordinary skill in the art that any number of array-processing stages may be implemented in alternative embodiments of the present invention.

It would be appreciated by one of ordinary skill in the art that the plurality of received sounds from BTE audio sensor 444 may also be treated as a sensor-specific directional sound signal in substantially the same manners as described above. It would also be appreciated that both coil audio sensor 442 and BTE audio sensor 444 may each be treated as single sensor by directional sound processor 484. In such an embodiment, directional sound processor 484 is configured to process the sensor-specific directional sound signals from audio sensors 444 and 442 to generate the directional sound signal therefrom.

It should also be appreciated that various combinations of acoustical transducers may be used for either BTE audio sensor 444 and/or coil audio sensor 442, and the configuration shown in FIG. 4 is merely illustrative. For example, it is within the scope of the invention that either sensor could comprise a single acoustical transducer while the other audio sensor comprises any number and type of acoustical transducers.

As noted above with reference to FIG. 3, BTE processor 426 is not limited to a BTE configuration as shown in FIG. 4. In alternative embodiments, for example, sound processor 426 may be a modular or a body worn sound processor.

Figure 5:
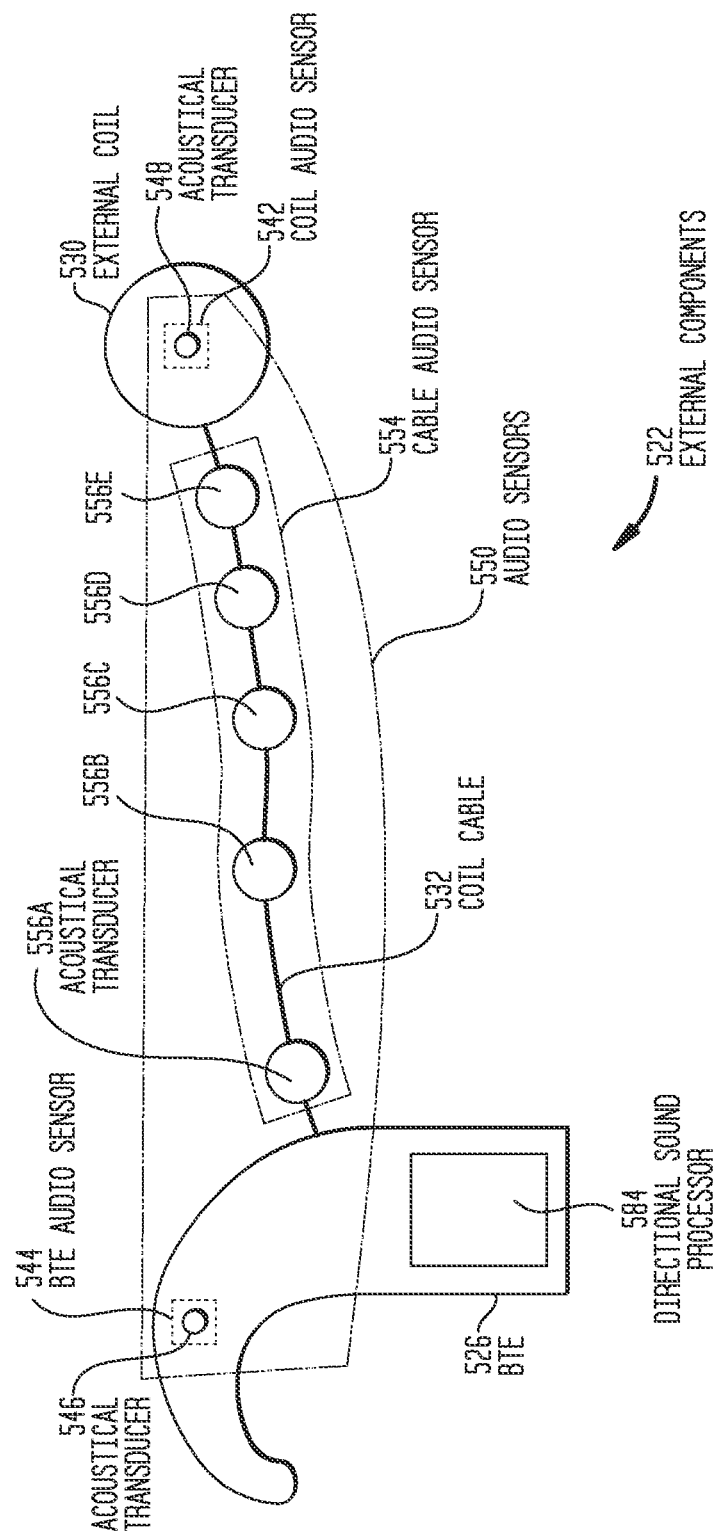
FIG. 5 is a simplified perspective view of the external components of a cochlear implant, in accordance with a further embodiment of the present invention.

FIG. 5 is a schematic diagram of another embodiment of external components 122 introduced above with reference to FIG. 1, referred to herein as external components 522. In the embodiment shown in FIG. 5, external components 522 comprise an embodiment of BTE sound processor 126, referred to herein as BTE 526 and an embodiment of external coil 130, referred to herein as external coil 530. BTE sound processor 526 is connected to external coil 530 via coil cable 532.

In this embodiment of the present invention, external components 522 comprise audio sensors 550 spatially-arranged across BTE 526, external coil 530 and cable 532 to receive ambient sounds. Audio sensors 550 residing on BTE 526 are collectively referred to as BTE audio sensor 544 while the acoustical transducers residing on external coil 530 are collectively referred to as coil audio sensor 542, and the acoustical transducers residing on cable 532 are collectively referred to as cable audio sensor 554.

BTE audio sensor 544 comprises one and preferably more acoustical transducers 546. The number of microphones in BTE sensor 544 may depend on various factors including the particular mechanical design of BTE 526, the particular type of technology used to realize acoustical transducers 546, and the desired characteristics of audio sensor 544.

Similarly, coil audio sensor 542 comprises one and preferably more acoustical transducers 548. Again, the number of acoustical transducers in coil audio sensor 542 may depend on various factors including but not limited to those noted above.

Cable audio sensor 554 comprises five acoustical transducers 556A-556E disposed along coil cable 532. Acoustical transducers 556 may be located at any position along cable 532. In one embodiment, acoustical transducers 556 have equidistant interstitial spacing while in other embodiments the interstitial spacing between neighboring acoustical transducers 556 varies. As with the other audio sensors, the quantity of acoustical transducers in coil cable sensor 554 may depend on various factors including but not limited to those noted above.

It should also be appreciated that one or more acoustical transducers 546, 548 and 556 may possess a directional or omni-directional polar response. In the illustrated embodiment, audio sensors 544, 542 and 554 are spatially-arranged to receive ambient sounds with their respective acoustical transducers 546, 548 and 556. In certain embodiments, each acoustical transducer 546, 548 and 556 transmits its received sounds to directional sound processor 584 in BTE 526. Directional sound processor 584 converts a plurality of received sounds into a stimulation instruction signal as described below with reference to FIG. 9.

In alternative embodiments, directional sound processor 584 may treat the acoustical transducers located in a particular sensor as a single sensor, as described above with reference to FIG. 4. As noted, in such an embodiment, the particular sensor, or the component on which the sensor is located, may further comprise an array-processing stage as described elsewhere herein. This additional array-processing stage may function substantially similar to the array-processing stages discussed below with reference to FIG. 9.

In the embodiment illustrated in FIG. 5, either one or more of BTE audio sensor 544, coil audio sensor 542, cable audio sensor 554, or any combination thereof may be treated as a single sensor, as described elsewhere herein. It should also be appreciated by one of ordinary skill in the art that the positions of BTE audio sensor 544, coil audio sensor 542, and cable audio sensor 554 nor their respective acoustical transducers 546, 548 and 556 are not restricted to the positions shown in FIG. 5. It should also be appreciated that various combinations of acoustical transducers may be implemented in BTE audio sensor 544, coil audio sensor 542 and/or cable audio sensor 554. As a result, the configuration shown in FIG. 5 is merely illustrative. For example, it is within the scope of the invention that any sensor could comprise a single microphone while the other sensors comprises any number of microphones. Furthermore, it is equally within the scope of the invention for all three of the sensors to comprise a single microphone. In addition, it would also be appreciated by one of ordinary skill in the art that audio sensors 550 may comprise any combination of BTE audio sensor 544, cable audio sensor 554, and coil audio sensor 542.

As noted above with reference to FIGS. 3 and 4, processor 526 is not limited to a BTE sound processor and may be any sound processor now or later developed. For example, processor 526 could be a modular processor.

Figure 6:
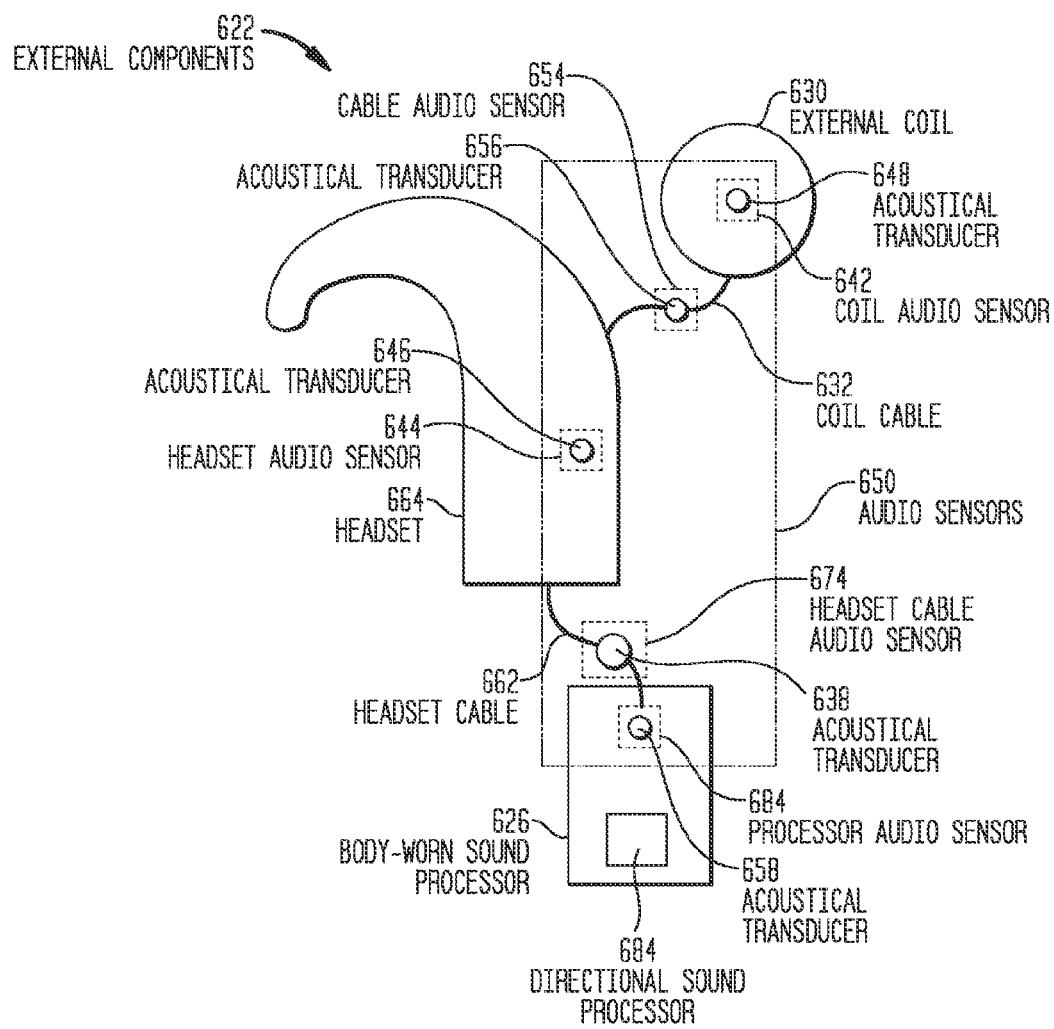
FIG. 6 is a simplified perspective view of the external components of a cochlear implant, in accordance with a still further embodiment of the present invention.

FIG. 6 is a schematic diagram of another embodiment of external components 122 introduced above with reference to FIG. 1, referred to herein as external components 622. In the embodiment shown in FIG. 6, external components 622 comprise a body-worn sound processor 626 implementing an embodiment of an directional sound processor 484 (referred to as 684), a headset 664, an embodiment of external coil 130, referred to herein as external coil 630, and a further embodiment of audio sensors 250, referred to herein as audio sensors 650. External coil 630 is connected to headset 664 via coil cable 632, while headset 664 is connected to processor 626 via headset cable 662.

Body-worn sound processor 626 is a sound processor worn on the recipient's body that contains all the physical elements that are required to process sound and generate an appropriate coded stimulation signal to send to external coil 630. Acoustical transducers of body worn sound processor are usually housed in headset component 664 that is operationally located behind the recipient's ear. Body-worn sound processor 626 acts as the main processing unit.

Audio sensors 650 comprise a plurality of sensors spatially-arranged to receive ambient sound. Audio sensors 650 may comprise any combination of a coil audio sensor 642, a cable audio sensor 654, a headset audio sensor 644, a headset cable sensor 674 or a processor sensor 684. Coil audio sensor 642 is similar to the coil audio sensor described above with reference to FIGS. 3-5. Coil audio sensor 642 is disposed on external coil 130 and may comprise one or more microphones 648. Similarly, cable audio sensor 654 is similar to the cable audio sensor described above with reference to FIG. 5. Cable audio sensor 654 is disposed on coil cable 632 connecting headset 664 and external coil 630, and may comprise one or more microphones 656.

Headset 664 is similar to a BTE in that it is constructed and arranged to fit behind the outer ear 112 of a recipient. However, unlike a BTE, headset 664 does not comprise the main processing means for external components 622.

Headset 664 further comprises a headset sensor 644. Headset sensor 644 comprises one or more acoustical transducers, referred to herein as microphones 646, disposed in headset 644. Microphones 646 may be disposed in headset 644 in a variety of positions. The number of microphones 646 in headset sensor 644 may depend on various factors including the particular mechanical design of headset 664, the particular type of technology used to realize microphones 646, and the desired characteristics of sensors 650.

Headset cable sensor 674 comprises one or more acoustical transducers 638 disposed along headset cable 662. Acoustical transducers 638 may be placed along the cable with equidistant spacing, or at varying spacing, as noted above. The number of acoustical transducers in headset cable sensor 674 may depend on various factors including but not limited to those noted elsewhere herein.

Processor audio sensor 684 is disposed on or in body-worn processor 626 and may comprise one or more acoustical transducers 658. Acoustical transducers 658 may be have a variety of configuration and may be located in a variety of positions. Accordingly, processor audio sensor 684 is not limited to the configuration shown in FIG. 6. The number of acoustical transducers 658 in processor audio sensor 684 may depend on various factors including but not limited to those noted elsewhere herein.

As in the other embodiments described herein, microphones 638, 646, 648, 656 and 658 may possess a directional or omni-directional polar response.

In the illustrated embodiment, ambient sounds are incident on sensors 650. Sensors 644, 642, 654, 674 and 684 are spatially-arranged to receive the ambient sounds with their respective acoustical transducers 646, 648, 656, 638 and 658. In certain embodiments, each acoustical transducer 646, 648, 654, 638 and 658 transmits its received sounds to directional sound processor 684 in body-worn sound processor 626. Directional sound processor 626 converts the plurality of acoustical signals from the audio sensors to a single stimulation instruction signal as described below with reference to FIG. 9.

In alternative embodiments, directional sound processor 684 may treat the acoustical transducers located in a particular sensor as a single sensor, as described above with reference to FIG. 4. As noted, in such an embodiment, the particular audio sensor and/or the component on which the sensor is located, further comprises an array-processing stage. This array-processing stage functions substantially similar to the array-processor discussed below with reference to FIG. 9.

In the embodiment illustrated in FIG. 6, either one or more of headset audio sensor 644, coil audio sensor 642, cable audio sensor 654, headset cable audio sensor 674, processor audio sensor 684, or any combinations thereof may be treated as a single sensor as described above.

It would be appreciated by one of ordinary skill in the art that the positions of headset audio sensor 644, coil audio sensor 642, coil cable audio sensor 654, processor audio sensor 684, and headset cable audio sensor 674 are not restricted to the positions shown in FIG. 6. It would also be appreciated that various combinations of microphones may be used for either headset audio sensor 644, coil audio sensor 642, coil cable audio sensor 654, processor audio sensor 684, and headset cable audio sensor 674. For example, it is envisioned that one or more sensors within sensors 650 may comprise a single microphone, while the other sensors comprise a plurality of microphones. Similarly, it is envisioned that all sensors in sensors 650 may comprise a single microphone.

Furthermore, it would be appreciated by one of ordinary skill in the art that various combinations may be used to for audio sensors 650. As a result, the configuration shown in FIG. 6 is merely illustrative. For example, it would be appreciated that one or more of headset sensor 644, coil sensor 642, coil cable sensor 654, processor sensor 684, or headset cable sensor 674 could be omitted from the configuration in various embodiments.

Figure 7:
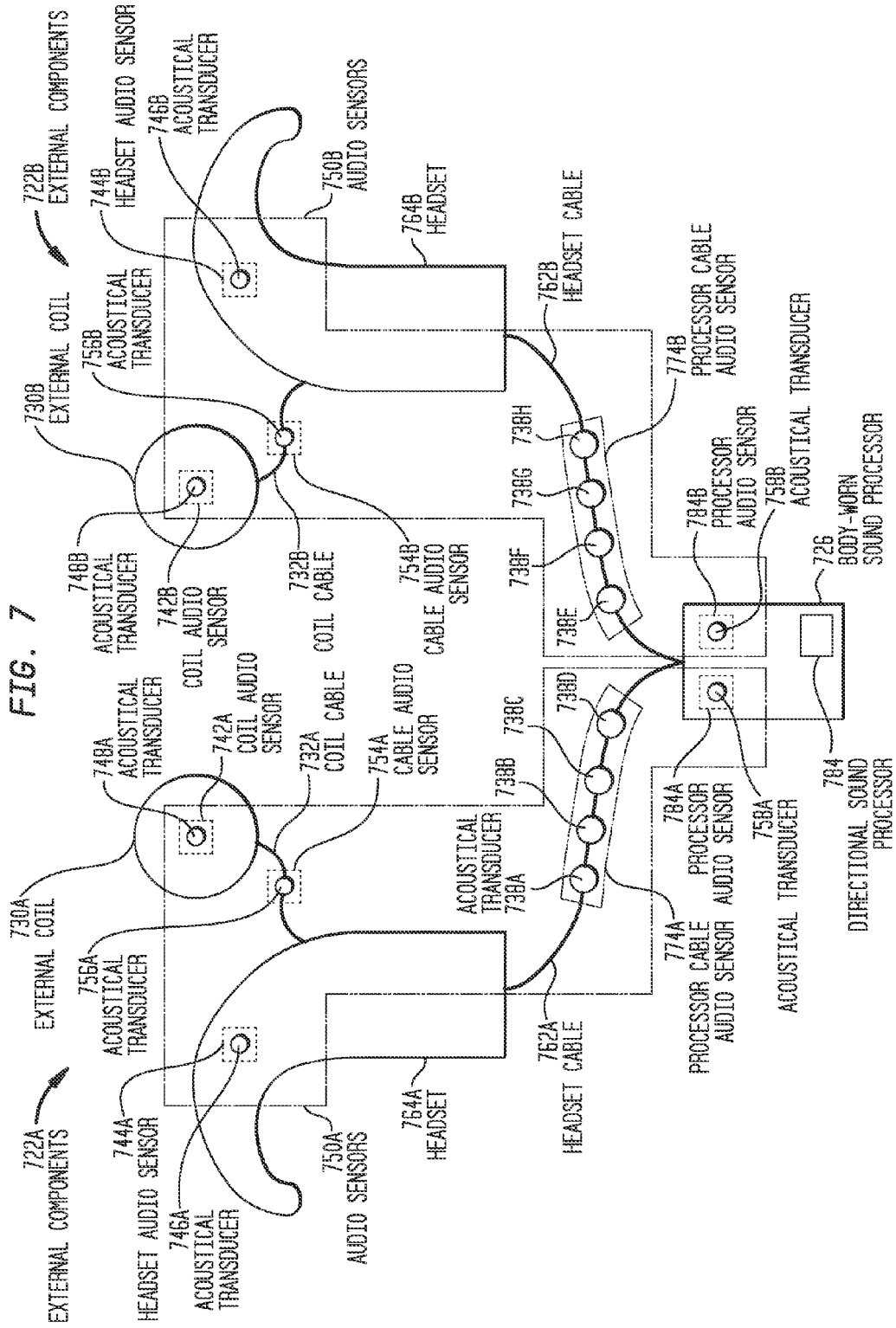
FIG. 7 is a simplified perspective view of the external components of a cochlear implant applicable to bilateral recipients, in accordance with an additional embodiment of the present invention.

FIG. 7 is a schematic diagram of the embodiment shown in FIG. 6 applicable to bilateral recipients. FIG. 7 illustrates two external components 722A and 722B. External components 722A and 722B are similar to the external components described above with reference to FIG. 6 in that each external component 722A and 722B comprises a headset 764A/764B, an external coil 730A/730B, and an embodiment of audio sensors 750A/750B. In the embodiment shown in FIG. 7, a body-worn sound processor 726 replaces sound processor 626 from FIG. 6. Sound processor 726 is connected to headsets 764A, 764B via headset cables 762A, 762B, respectively.

In the embodiment shown in FIG. 7, body-worn sound processor 726 comprises one or more sound processors. In one particular embodiment, body-worn sound processor 726 comprises two sound processors. In this embodiment, each sound processor is connected to one headset 764. In another embodiment, body-worn sound processor 726 comprises a single sound processor connected to both headsets 764 configured to generate stimulation instruction signals for each implant.

In further embodiments, directional sound processor 784 is configured to treat one or more audio sensors on external components 722A and 722B as a single sensor. For example, in such an embodiment, directional sound processor 784 is configured to treat a plurality of sounds received from processor cable audio sensors 774A and 774B as a single received sound input. An advantage of this configuration is that using microphone signals captured from each side of the head resembles normal hearing more closely than when using microphone signals captured from one side of the head. Processor cable sensors 774 may comprise additional array-processing stages as described above with reference to FIG. 4. In other embodiments, directional sound processor 784 may comprise a plurality of array-processing stages as described above.

Despite the type of body-worn sound processor 726 used, external components 722A and 722B will each comprise audio sensors 750 that are substantially similar to audio sensors 650 described above. As such, audio sensors 750 may comprise any combination of a coil audio sensor 742, coil cable audio sensor 754, headset audio sensor 744, headset cable audio sensor 774 or processor audio sensor 784. Coil audio sensor 742, coil cable audio sensor 754, headset audio sensor 744 and headset cable audio sensor 774 each comprise one or more acoustical transducers and are substantially the same as discussed above with reference to FIGS. 3-6.

Processor audio sensors 784 are disposed in body-worn sound processor 726 and each comprises one or more acoustical transducers 758. Acoustical transducers 758 may be placed in various positions or configurations in body-worn sound processor 726. The number of acoustical transducers in each processor audio sensor 784 may depend on various factors including but not limited to those noted above.

In embodiments of the present invention, microphones 738, 746, 748, 756 and 758 may possess a directional or omni-directional polar response.

In the illustrated embodiment, ambient sounds are incident on sensors 750. Audio sensors 744, 742, 754, 774 and 784 are spatially-arranged to receive the ambient sound signals with their respective acoustical transducers 746, 748, 756, 738 and 758. In certain embodiments, each acoustical transducer 746, 748, 756, 738 and 758 transmits its received sounds to directional sound processor 784 in body-worn speech processor 726. Directional sound processor 784 then converts the plurality of received sounds into a single stimulation instruction signal as described below with reference to FIG. 9.

In alternative embodiments, directional sound processor 784 may treat the acoustical transducers located in a particular audio sensor as a single sensor, as described above with reference to FIG. 4. As noted, in such an embodiment, the particular sensor, or the component on which the sensor is located, further comprises an array-processing stage. This array-processing stage functions substantially similar to the array-processor discussed below with reference to FIG. 9.

In the embodiment illustrated in FIG. 7, either one or more of headset audio sensors 744, coil audio sensors 742, cable audio sensors 754, headset cable audio sensors 774, processor audio sensors 784, or any combinations thereof may be treated as a single audio sensor as described above.

It should further be appreciated by one of ordinary skill in the art that the positions of headset audio sensors 744, coil audio sensors 742, coil cable audio sensors 754, processor audio sensors 784, and headset cable audio sensors 774, and their respective acoustical transducers, are not restricted to the positions shown in FIG. 7.

It should further be appreciated that various combinations of acoustical transducers may be used for either headset audio sensors 744, coil audio sensors 742, coil cable audio sensors 754, processor audio sensors 784, and headset cable audio sensors 774. For example, it is envisioned that one or more audio sensors within sensors 750 comprises a single microphone or other type acoustical transducer, while the other audio sensors comprise a plurality of microphones or other type of acoustical transducer. Similarly, it is envisioned that all audio sensors 750 may comprise a single microphone or other type of acoustical transducer.

Furthermore, it would be appreciated by one of ordinary skill in the art that various combinations of acoustical transducers may be used to form audio sensors 750. For example, it would be appreciated that one or more of headset audio sensors 744, coil audio sensors 742, coil cable audio sensors 754, processor audio sensors 784, or headset cable audio sensors 774 could be omitted from the configuration in various embodiments.

Figure 8:
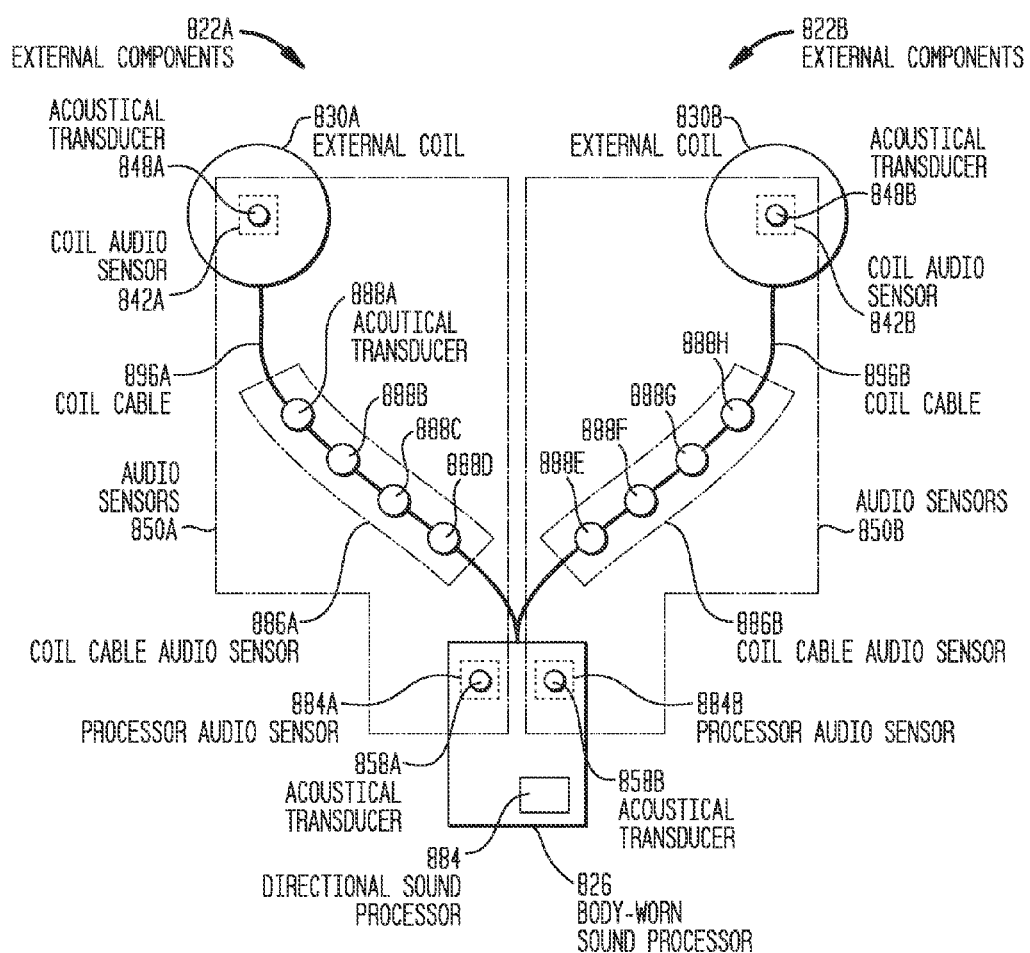
FIG. 8 is a simplified perspective view of the external components of a cochlear implant applicable to bilateral recipients, in accordance with a still further embodiment of the present invention.

FIG. 8 is an illustration of another embodiment of the present invention applicable to bilateral recipients. FIG. 8 illustrates two external components 822A and 822B. In the embodiment shown in FIG. 8, external components 822A and 822B each comprise an external coil 830 and an embodiment of sensors 250, referred to as audio sensors 850. Each external coil 830 is connected to body-worn sound processor 826 via its respective coil cable 896.

External coils 830 are similar to external coils 130 described above; as such, external coils 830 also comprise a coil audio sensor 842. As with the other embodiments described herein, external coils 830 may contain hardware that partially or fully processes received sounds before transferring the sounds to body-worn sound processor 826.

As shown in FIG. 8, body-worn sound processor 826 comprises one or more sound processors. In one particular embodiment, body-worn sound processor 826 comprises two sound processors. In this embodiment, each sound processor is connected to one external coil 830. In another embodiment, body-worn sound processor 826 comprises a single sound processor connected to both external coils 830 configured to provide a stimulation instruction signal to each implant.

Sensors 850 may comprise any combination of a coil sensor 842, a coil cable sensor 886 or a processor sensor 884. Coil sensor 842 is similar to the coil sensor discussed above with reference to FIGS. 3-7. Similarly, coil cable sensor 886 is similar to the coil cable sensors discussed above with reference to FIGS. 5-7. Each coil cable sensor 886 is disposed on coil cable 896 connecting external coil 830 and body-worn sound processor 826, and may comprise one or more microphones 888. Microphones 888 are disposed along coil cable 896 with equidistant spacing, or at varying spacing.

Processor sensors 884 are disposed in body-worn sound processor 826 and may comprise one or more microphones 858. Microphones 858 may be in body-worn sound processor 826 in a variety of positions and configurations and is not limited to the configurations shown in FIG. 8. The number of microphones 858 in processor sensors 884 may depend on various factors including the particular mechanical design of body-worn sound processor 826, the particular type of technology used to realize microphones 858, and the desired characteristics of sensors 850.

In embodiments of the present invention, microphones 848, 858 and 888 may possess a directional or omni-directional polar response.

In the illustrated embodiment, ambient sounds are incident on sensors 850. Sensors 842, 884 and 886 are spatially-arranged to receive the ambient sounds with their respective microphones 848, 858 and 888. In certain embodiments, each microphone 848, 858 and 888 transmits its received sounds to directional sound processor 884 in body-worn speech processor 826. Directional sound processor 884 then converts the plurality of received sounds into a single stimulation instruction signal as described below with reference to FIG. 9.

In alternative embodiments, directional sound processor 884 may treat the microphones located in a particular sensor as a single sensor, as described above with reference to FIG. 4. As noted, in such an embodiment, the particular sensor, or the component on which the sensor is located, further comprises an array-processing stage. This array-processing stage functions substantially similar to the array-processing stages discussed below with reference to FIG. 9.

In the embodiment illustrated in FIG. 8, either one or more of coil sensors 842, coil cable sensors 886 or processor sensors 884, or any combinations thereof may be treated as a single sensor as described above.

It would be appreciated by one of ordinary skill in the art that the positions of coil sensors 842, coil cable sensors 886, processor sensors 884 are not restricted to the positions shown in FIG. 8. It would also be appreciated that various combinations of microphones may be used for either coil sensors 842, coil cable sensors 886, processor sensors 884. For example, it is envisioned that one or more sensors within sensors 850 could comprise a single microphone, while the other sensors comprise a plurality of microphones. Similarly, it is envisioned that all sensors in sensors 850 could comprise a single microphone.

Furthermore, it would be appreciated by one of ordinary skill in the art that various combinations may be used to make up sensors 850. As a result, the configuration shown in FIG. 8 is merely illustrative. For example, it would be appreciated that one or more of coil sensors 842, coil cable sensors 886, processor sensors 884 could be omitted from the configuration in various embodiments.

It would also be appreciated that the above described embodiment is equally applicable to a recipient with a single implant. In such an embodiment, only one set of external components 822 would be used. In such an embodiment, body-worn sound processor 826 would comprise a single sound processor 884.

It should be appreciated by one of ordinary skill in the art that the acoustical transducers utilized in the embodiments described herein with reference to FIGS. 3-8 may be any acoustical transducers now or later developed that receives as an input an acoustic signal and that converts that signal to an electrical form, either analog or digital, for further processing. The acoustical transducers of the present invention are not limited to any particular type of technology known or later developed. For example, the acoustical transducers may be realized using electret condenser technology or MEMS (Micro-Electro-Mechanical-Systems) technology.

Furthermore, in the embodiments described above with reference to FIGS. 3-8, the transmission of sounds and signals may be accomplished through wireless transmission as well as through cables connecting various components. Although the various embodiments have been illustrated with cables connecting the various components, embodiments that do not require cables are equally within the scope of the invention.

Embodiments of directional sound processor 284 are described next below with reference to FIG. 9. As noted, in each exemplary embodiment of audio sensors 250 described above with reference to FIGS. 3 through 8, the embodiment of directional sound processor 284 implemented in such embodiments, was referenced by a unique reference number 384, 484, 584, 684, 784 and 884, respectively. The embodiments of directional sound processor 284 described next below may be implemented as any one of such embodiments.

As shown in FIG. 2, directional sound processor 284 comprises an array processor 280 and a conventional sound processor 282. As noted, array-processing, also commonly referred to as beamforming, refers to the field of sound processing utilizing an array of audio sensors that are spatially-arranged to receive ambient sounds. Array-processing creates a beam pattern, that is more directive or sensitive to sounds propagating from a desired direction, compared to the directivity or sensitivity of an individual sensor receiver alone. In other words, array processing increases the signal-to-noise ratio (SNR) for sounds sensed from a desired direction while sounds sensed from other directions will be attenuated. The desired direction can be at a fixed angle or determined based on, for example, the amplitudes of the incident ambient sounds.

Figure 9:
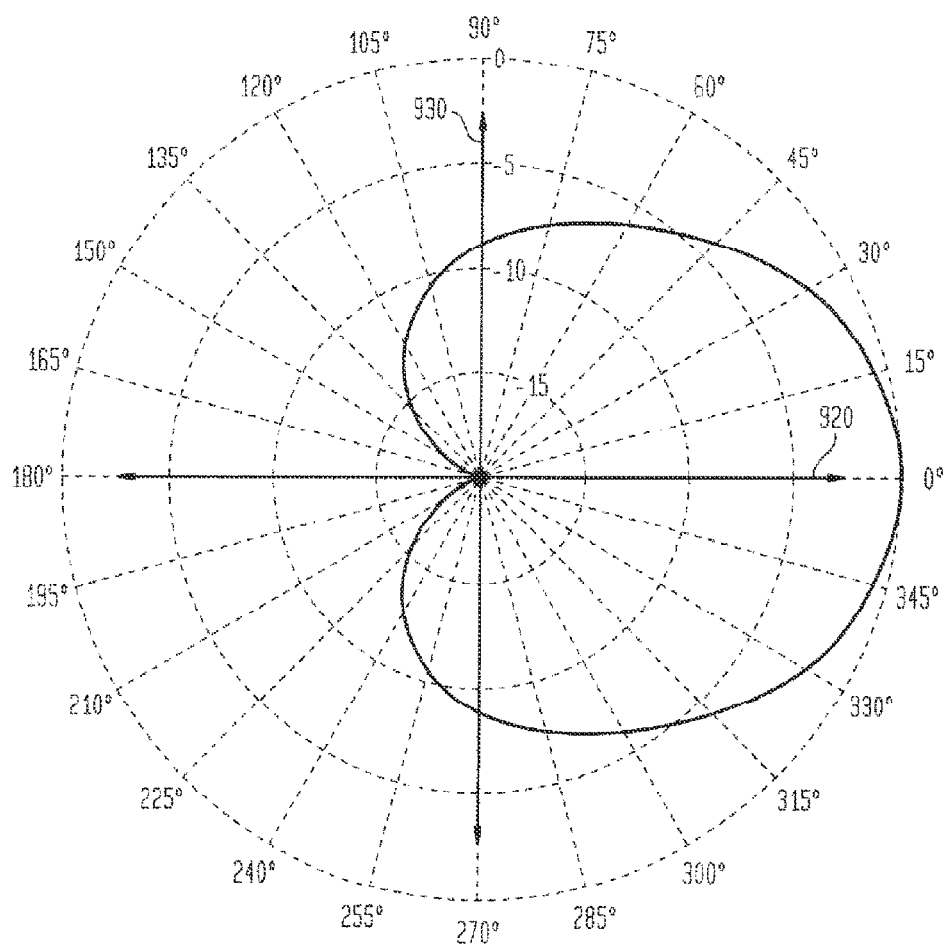
FIG. 9 is a beam pattern generated by the array-processing algorithms in accordance with the embodiment of the invention illustrated in FIG. 3.

FIG. 9 illustrates a beam pattern created by the array-processing of the present invention. The term beam pattern refers to how the sensitivity of a set of audio sensors vary in three dimensions to sounds propagating toward the sensors from any direction. The beam pattern indicates how well a sound signal from a given direction will be attenuated relative to the maximum sensitivity of the array. A null in the beam pattern is a location where the sensitivity of the array has been significantly reduced, indicating that a sound signal propagating toward the array from that direction will be attenuated relative to sounds propagating toward the array from the desired direction. Nulls are desirable characteristics, and in array-processing algorithms it is possible to steer nulls toward specific directions and thereby attenuate interfering signals by using delay and sum techniques or adaptive noise cancellation techniques for example.

In FIG. 9, a sound is received at two microphones in accordance with the embodiment of the present invention illustrated in FIG. 3. The beam pattern shown in FIG. 9 is taken along a single horizontal plane. The array-processing of this embodiment creates a null along axis 920 which is at 180 degrees from the direction of maximum sensitivity. The system has maximum sensitivity to sounds propagating towards the array along axis 920 from the zero-degree direction. The array-processor interprets such sounds as desired sounds, while sounds received from other directions are interpreted as noise signals. The array-processing algorithms mathematically combine sounds propagating along or near axis 920 from the zero degree direction into the directional sound signal while eliminating the noise signals. It should also be noted that the array processing algorithms are not limited to directions of maximum sensitivity.

Several types of array-processing algorithms may be used to convert a plurality of sounds received by the audio sensors into a directional sound signal. For example, in one embodiment, the array-processing algorithm that is used is of the type as described in *Blind Beamforming on a Randomly Distributed Sensors System*, Kung Yao et. al., 1998 IEEE Journal on Selected Areas in Communications, Vol. 16, No 8, which is hereby incorporated by reference herein. Such an algorithm as described in this reference may be usefully applied to enable a random distribution of sensors and microphones to be used. With a random distribution of sensors and microphones, the location of each cannot be known exactly due to anatomical differences between recipients. However, the use of adaptive algorithms and source localization algorithms such as blind beamforming can overcome this issue.

In such an embodiment, it is not necessary for the array-processing algorithms to be provided with the exact location of each acoustical transducer or sensor. From the group of individual input signals from each acoustical transducer, directional sound processor 284 calculates an ensemble averaged correlation matrix of the received sensor data vector to determine the source of the highest peak power spectral density. The array weights are obtained from the dominant eigenvector of a matrix eigenvalue problem.

In an alternative embodiment, an array-processing algorithm may be implemented which relies upon known spatial dimensions between each one of the sensors or acoustical transducers. This type of array-processing algorithm may be of the type described in U.S. Pat. No. 6,888,949, which is hereby incorporated by reference herein. Similarly, the array-processing algorithm of this embodiment could be of the type described in WO 2005/006808, which is hereby incorporated by reference herein.

Further embodiments of array-processor 280 may use noise canceling adaptive filtering within the array-processing algorithm. In such an embodiment, the adaptive algorithm would use a noise reference signal as part of the processing scheme. A particular sensor is chosen as the sensor to receive a noise reference signal. In one particular embodiment, the coil sensor is chosen as the sensor that provides the noise reference signal. The coil sensor is chosen because the physical location of the transmitter coil on the recipient's head lends itself to providing a better noise reference to the array-processing algorithms, given its proximity to noise signals propagating from the rear of the recipient. The difference in amplitudes of the noise signals received by the coil sensor and other microphones will be more pronounced, making the signal from the coil sensor better suited to be a noise reference, given that the desired signal the recipient wishes to hear typically propagates toward the sensors from the front of the recipient.

As noted, FIG. 9 illustrates the beam pattern resulting from the use of two microphones, similar to the embodiment illustrated in FIG. 3. The use of additional sensors and microphones, as described with reference to FIGS. 4-8 extends the array of sensors, thereby increasing the array aperture and making the beam pattern more directional. The larger the aperture of the sensors, the better the resolution of the sensors, and hence the greater the flexibility to tailor the beam pattern. Resolution corresponds to the width of the main beam in the beam pattern. A decrease in the width of the main beam results in increased directivity in the desired direction and greater noise reduction in the other directions. Furthermore, there is no need for the sensors to be positioned in a symmetrical pattern.

In still further embodiments, the varying of the spacing between the microphones in a sensor results in tailoring of the array-processing algorithms to receive signals of particular frequencies more optimally. Recall that low frequency signals have large wavelengths. This means the microphone elements should be placed further apart than for high frequency signals in order to better discriminate the low frequency signal.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any discussion of documents, acts, materials, devices, articles or the like which has been included in the present specification is solely for the purpose of providing a context for the present invention. It is not to be taken as an admission that any of these matters form part of the prior art or were common general knowledge in the field relevant to the present invention as it existed before the priority date of each claim of this application.

What is claimed is:

1. A prosthetic hearing implant comprising:
   first and second sound processing units, wherein said first sound processing unit is configured to communicate with said second sound processing unit, and is further configured to transmit signals to at least one internal component of said prosthetic hearing implant;
   a plurality of spatially-arranged audio sensors, including first and second audio sensors, configured to receive ambient sound, and comprising at least one sensor located in said first sound processing unit and at least one sensor located in said second sound processing unit; and
   at least one directional sound processor having an array-processing stage configured to generate a directional sound signal from sound received by the first one of said plurality of sensors, and wherein said directional sound processor is configured to combine said directional sound signal and a signal representative of sound received by the second one of said plurality of sensors to generate a processed sound signal from which sound received from non-desired directions is attenuated.

2. The prosthetic hearing implant of claim 1, further comprising a cable and a transmit unit connected to said first sound processing unit by said cable wherein each of the first sound processing unit, the cable and the transmit unit are comprised in a single cochlear implant.

3. The prosthetic hearing implant of claim 1, wherein each of said plurality of sensors comprises at least one acoustical transducer.

4. The prosthetic hearing implant of claim 1, wherein one or more of said plurality of sensors each comprise a plurality of acoustical transducers.

5. The prosthetic hearing implant of claim 1, wherein said directional sound signal is an enhanced representation of said sound received by said first one of said sensors from one or more desired directions.

6. The prosthetic hearing implant of claim 5, wherein said one or more desired directions are determined based on the amplitudes of the incident ambient sounds.

7. The prosthetic hearing implant of claim 1, wherein at least one the plurality of spatially-arranged audio sensors is located in an external component of the prosthetic hearing implant.

8. The prosthetic hearing implant of claim 3, wherein said array-processing stage is configured to generate said directional sound signal from sound received by said one or more acoustical transducers.

9. The prosthetic hearing implant of claim 8, wherein said directional sound processor further comprises:
   at least a second array-processing stage configured to generate a second directional sound signal from said sound received by said second one of said plurality of sensors wherein said second directional sound signal is representative of sound received by said second one of said plurality of sensors.

10. The prosthetic hearing implant of claim 1, wherein said directional sound processor generates said directional sound signal from signals received from both the sensor located in said first sound processing unit and the sensor located in said second sound processing unit.

11. The prosthetic hearing implant of claim 2, wherein said first sound processing unit is configured to communicate with said second sound processing unit via a cable.

12. The prosthetic hearing implant of claim 1, wherein said first sound processing unit is configured to communicate with said second sound processing unit wirelessly.

13. The prosthetic hearing implant of claim 1, wherein said directional sound processor is a body-worn sound processor.

14. The prosthetic hearing implant of claim 1, wherein said directional sound processor is located in said first sound processing unit.

15. A method for delivering stimulation signals to a recipient's cochlea, wherein the stimulation signals represent sound received from a desired direction, the method comprising:
   receiving ambient sounds at two or more audio sensors spatially-arranged on a plurality of external components of a prosthetic hearing implant, wherein said external components include a first sound processing unit and a second sound processing unit; and
   processing sound received, by at least one audio sensor on said first sound processing unit and at least one audio sensor on said second sound processing unit, from a desired direction,
   wherein said processing sound comprises attenuating sound received from directions other than said desired direction.

16. The method of claim 15, wherein said processing sound received from a desired direction and attenuating sound received from other directions further comprises:
   generating a directional sound signal by enhancing the sensitivity of the prosthetic hearing implant to sounds from desired directions.

17. The method of claim 15, further comprising:
   converting said directional sound signal to a stimulation instruction signal.

18. The method of claim 15, wherein at least one of said audio sensors comprises at least one acoustical transducer configured to generate sound signals from received ambient sounds.

19. The method of claim 18, wherein generating a directional sound signal further comprises:
   receiving ambient sounds at each sensor with one or more acoustical transducers;
   generating a sensor specific directional sound signal from sounds received by said transducers in a single sensor; and
   generating said directional sound signal based on one or more of said sensor specific directional sound signals and one or more other received sounds.

20. The method of claim 15, wherein said first sound processing unit wirelessly communicates with said second sound processing unit.

* * * * *